United States Patent
Santore et al.

(10) Patent No.: US 11,167,286 B2
(45) Date of Patent: Nov. 9, 2021

(54) SENSORS AND METHODS FOR CAPTURING TARGETED CELLS

(71) Applicant: The University of Massachusetts, Boston, MA (US)

(72) Inventors: Maria M. Santore, Sunderland, MA (US); Kathleen Arcaro, Leverett, MA (US); Surachate Kalasin, Chicopee, MA (US)

(73) Assignee: THE UNIVERSITY OF MASSACHUSETTS, Boston, MA (US)

( * ) Notice: Subject to any disclaimer, the term of this patent is extended or adjusted under 35 U.S.C. 154(b) by 0 days.

(21) Appl. No.: 14/844,834

(22) Filed: Sep. 3, 2015

(65) Prior Publication Data

US 2016/0069861 A1    Mar. 10, 2016

Related U.S. Application Data

(60) Provisional application No. 62/045,885, filed on Sep. 4, 2014.

(51) Int. Cl.

| | |
|---|---|
| *B01L 3/00* | (2006.01) |
| *G01N 15/10* | (2006.01) |
| *G01N 33/543* | (2006.01) |
| *G01N 15/00* | (2006.01) |

(52) U.S. Cl.
CPC ........ *B01L 3/502761* (2013.01); *G01N 15/10* (2013.01); *G01N 33/54366* (2013.01); *B01L 2200/0668* (2013.01); *B01L 2300/0627* (2013.01); *B01L 2300/16* (2013.01); *G01N 2015/008* (2013.01); *G01N 2015/0065* (2013.01); *G01N 2015/1006* (2013.01)

(58) Field of Classification Search
CPC ....... B01L 3/502761; B01L 2200/0668; B01L 2300/0627; B01L 2300/16; G01N 15/10; G01N 2015/1006; G01N 2015/0065; G01N 2015/008; G01N 33/54366
See application file for complete search history.

(56) References Cited

U.S. PATENT DOCUMENTS

| | | |
|---|---|---|
| 8,382,858 B2 | 2/2013 | Santore et al. |
| 2010/0009379 A1 | 1/2010 | Santore et al. |

OTHER PUBLICATIONS

Faupel-Badger (Badger) "Postpartum Remodeling, Lactation, and Breast Cancer Risk: Summary of a National Cancer Institute—Sponsored Workshop" Journal of the National Cancer Institute Advance Access published Dec. 21, 2012 p. 1-9.*

Zhang et al. "Zeta potential: a surface electrical characteristic to probe the interaction of nanoparticles with normal and cancer human breast epithelial cells" Biomed Microdevices (2008) 10:321-328.*

Santore et al. "Beyond Molecular Recognition: Using a Repulsive Field to Tune Interfacial Valency and Binding Specificity between Adhesive Surfaces".*

Wong et al. "Quantitative analysis of promoter methylation in exfoliated epithelial cells isolated from breast milk of healthy women" Epigenetics 5:7, 645-655; Oct. 1, 2010.*

Wikipedia downloaded at https://en.wikipedia.org/wiki/Polyethylene_glycol, pp. 2-9.*

Fang et al.; "Bacterial Adhesion on Hybrid Cationic Nanoparticle-Polymer Brush Surfaces: Ionic Strength Tunes Capture From Monovalent to Multivalent Binding"; Colloids and Surfaces B: Biointerfaces, vol. 87; 2011; pp. 109-115.

Fang et al.; "Using Flow to Switch the Valency of Bacterial Capture on Engineered Surfaces Containing Immobilized Nanoparticles"; American Chemical Society, Langmuir Article, vol. 28; 2012; pp. 7803-7810.

Gon et al.; "Interaction of Cationic Proteins and Polypeptides with Biocompatible Cationically-Anchored PEG Brushes"; American Chemical Society, Macromolecules Article, vol. 44; 2011; pp. 8161-8168.

Gon et al.; "Manipulating Protein Adsorption Using a Patchy Protein-Resistant Brush"; American Chemical Society, Langmuir Article, vol. 26, No. 14; 2010; pp. 12147-12154.

Gon et al.; "Sensitivity of Protein Adsorption to Architectural Variations in a Protein-Resistant Polymer Brush Containing Engineered Nanscale Adhesive Sites"; American Chemical Society, Langmuir Article, vol. 27; 2011; pp. 15083-15091.

Gon et al.; "Single Component and Selective Competitive Protein Adsorption in a Patchy Polymer Brush: Opposition between Steric Repulsions and Electrostatic Attractions"; American Chemical Society, Langmuir Article, vol. 27, No. 4; 2011; pp. 1487-1493.

Gozgit et al.; "PLD1 is overexpressed in an ER-negative MCF-7 cell line variant and a subset of phospho-Akt-negative breast carcinomas"; British Journal of Cancer, vol. 97, Issue No. 6; 2007; pp. 809-817.

* cited by examiner

*Primary Examiner* — Blaine Lankford
(74) *Attorney, Agent, or Firm* — Cantor Colburn LLP

(57) ABSTRACT

A sensor for selectively capturing a targeted cell type in a fluid includes an engineered surface. The engineered surface includes a substrate, a non-adhesive element disposed on at least a portion of a substrate, and an adhesive element disposed on the substrate. The sensor also includes a flow channel in operative contact with the engineered surface; and a detector configured to detect the targeted cell type captured on the engineered surface. Also described is a method for selectively capturing target cell types using the engineered surface.

38 Claims, 2 Drawing Sheets

SENSORS AND METHODS FOR CAPTURING TARGETED CELLS

CROSS REFERENCE TO RELATED APPLICATIONS

This application claims the benefit of U.S. Provisional Application Ser. No. 62/045,885, filed Sep. 4, 2014, which is incorporated by reference herein in its entirety.

STATEMENT OF FEDERALLY SPONSORED RESEARCH

This invention was made with U.S. Government support under Grant Number CA159109-01A1, which was awarded by the National Institute of Health (NIH). The U.S. Government has certain rights in this invention.

TECHNICAL FIELD

This application relates to sensors and methods for the selective capture of target cells from fluids comprising non-target cells and other substances.

BACKGROUND OF THE INVENTION

Selective harvesting and concentrating epithelial cells from body fluids will play a significant role in early detection and treatment of various carcinomas. However, selectively capturing and concentrating target cell types, such as epithelial cells, from a fluid of biological origin is a challenging task.

Breast cancer, which accounts for about 25% of all cancers in women, could be better combated using an early risk assessment methods. For example, methylation patterns in the DNA of exfoliated breast epithelial cells in the milk of women after childbirth may be a highly accurate molecular-based risk indicator. Such method requires enrichment of epithelial cells. However, harvesting and concentrating epithelial cells from breast milk is a costly and time consuming task, because milk contains comparable numbers of leukocyte and epithelial cells, and milk also contains proteins, fats, and salts.

Current methods of cell enrichment rely extensively on biomolecular targeting, for instance immobilized antibodies. Also, currently available methods typically involve expensive instrumentation (e.g., flow cytometry, cell sorting), and require highly-skilled technicians. Therefore, there is a need for new type of sensors and methods for selectively capturing targeted cell types (for example, epithelial cells) which are cheaper, reliable, and easier to use, for instance at the point of care.

SUMMARY

In an embodiment, there is provided a sensor for selectively capturing a targeted cell type in a fluid comprising a non-targeted cell, the sensor comprising an engineered surface comprising a substrate, a non-adhesive element disposed on at least a portion of a substrate, and an adhesive element disposed on the substrate; a flow channel in operative contact with an engineered surface; and a detector configured to detect the targeted cell type captured on the engineered surface.

In another embodiment, there is provided a method of selectively capturing a targeted cell type in a fluid comprising a non-targeted cell, the method comprising providing an engineered surface comprising a substrate, a non-adhesive element disposed on at least a portion of a substrate, and an adhesive element disposed on the substrate; and contacting the fluid with the engineered surface under conditions effective to adhere at least a portion of the targeted cell type in the fluid to the engineered surface.

In a more specific embodiment, a sensor for selectively capturing a targeted epithelial cell type, specifically a breast epithelial cell, in a fluid that includes a non-targeted cell type is described, where the sensor comprises an engineered surface comprising a substrate, a non-adhesive polymer brush element disposed on at least a portion of a substrate, and an adhesive element disposed on the substrate; a flow channel in operative contact with an engineered surface; and a detector configured to detect the targeted cell type captured on the engineered surface.

In another more specific embodiment, a method of selectively capturing a targeted epithelial cell type, specifically a breast epithelial cell, in a fluid that includes a non-targeted cell is described, where the method comprises providing an engineered surface comprising a substrate, a non-adhesive polymer brush element disposed on at least a portion of a substrate, and an adhesive element disposed on the substrate; contacting the fluid with the engineered surface under conditions effective to adhere at least a portion of the targeted cell type in the fluid to the engineered surface.

The above described and other embodiments are described in detail below.

BRIEF DESCRIPTION OF THE DRAWINGS

The following Figures are exemplary embodiments, which do not limit the claims.

DETAILED DESCRIPTION OF THE INVENTION

Figure 1:
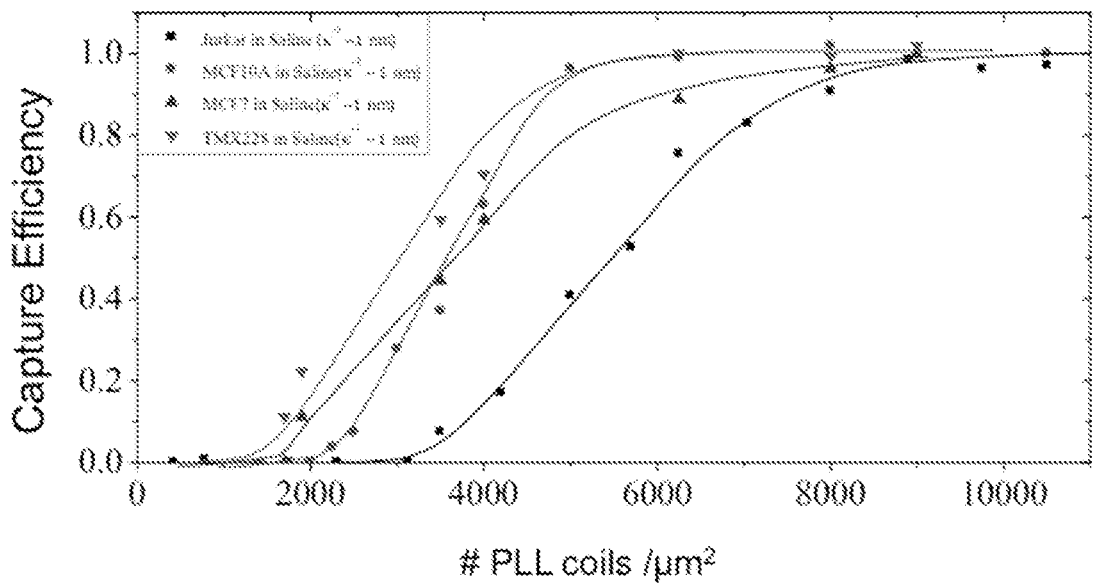
FIG. 1 is a plot of efficiencies of capturing cells from buffered suspensions of single cell types as a function of the surface density of PLL coils on the collector.

As used herein, the term "selectivity" refers to amount of targeted material captured on the engineered surface divided by the amount of untargeted material captured on the engineered surface, further divided by the amount of targeted material per unit volume in the original solution divided by the amount of untargeted material per unit volume in the original solution. The amount of material may be represented as number of cells.

The present inventors have demonstrated that engineered surfaces capable of selectively capturing target cells can be prepared based on careful design and selection of synthetic polymers and appropriate substrates. A unique feature of the present engineered surfaces is that they do not rely on bio-molecular recognition for capturing the target cells. The present inventors demonstrated that it was possible to selectively capture targeted cells from a buffer, and to selectively capture targeted cells in the presence of the breast milk serum. The present inventors also surprisingly found that some engineered surfaces exhibit selective capture that was tunable with flow rates.

In some embodiments, there is provided a sensor for selectively capturing a targeted cell type in a fluid comprising a non-targeted cell, the sensor comprising an engineered surface comprising a substrate, a non-adhesive element disposed on at least a portion of a substrate, and adhesive elements disposed on the substrate; a flow channel in operative contact with an engineered surface; and a detector configured to detect the targeted cell type captured on the engineered surface.

In other embodiments, there is provided a method of selectively capturing a targeted cell type in a fluid comprising a non-targeted cell, the method comprising providing an engineered surface comprising a substrate, a non-adhesive element disposed on at least a portion of a substrate, and an adhesive element disposed on the substrate; contacting the fluid with the engineered surface under conditions effective to adhere at least a portion of the targeted cell type in the fluid to the engineered surface.

The adhesive element chemical composition, the non-adhesive element chemical composition, and the non-adhesive element molecular weight are suitably selected based on the type of the targeted cell that is intended to be captured using the sensor and/or the method of the above embodiments. Further, the wall shear rate at which the fluid is contacted with the engineered surface is suitably selected based on the targeted cell type.

In some embodiments, the sensor or the method comprises selecting a wall shear rate within a range of 10 to 500 $s^{-1}$, preferably about 10 to about 30 $s^{-1}$, the adhesive element chemical composition, the non-adhesive element chemical composition, and the non-adhesive element molecular weight effective to capture the target cell, wherein a ratio of target cells to non-target cells captured varies with wall shear rate at which the target cells are contacted with the engineered surface.

The wall shear rate at which the fluid is contacted with the engineered surface may be suitably selected from the range of about 10 to about 500 $s^{-1}$. Within the range of 10 to 500 $s^{-1}$, the shear rate can be about 10 to about 400 $s^{-1}$, the shear rate can be about 10 to about 300 $s^{-1}$, the shear rate can be about 10 to about 200 $s^{-1}$, specifically, the shear rate can be about 10 to about 100 $s^{-1}$, and specifically the shear rate can be about 10 to about 30 $s^{-1}$.

The target cell type may be any suitable cell type of biological origin. The targeted cell type can be from a patient or from primary culture, or it may be an immortalized cell line. In some embodiments, the targeted cell-type is an epithelial cell type or a leukocyte. The targeted cell type may comprise primary epithelial cells or primary leukocyte cells. In some particular embodiments, the target cell type comprises epithelial cells.

In some embodiments, the target cells comprise epithelial cells and a lower shear rate is a selected for selectively capturing the epithelial cells. In other embodiments, the target cells comprise lymphocyte cells and a high shear rate is a selected for selectively capturing the lymphocyte cells.

The substrate can be of any material compatible with the intended use of the sensor and the method, for example a glass, a synthetic polymer, a natural polymer, a metal, a metal oxide, a ceramic, or a combination comprising at least one of the foregoing materials. The substrate can further be of any shape or configuration compatible with the intended use of the methods, for example flat, contoured, a fiber, or a combination comprising at least one of the foregoing shapes.

The non-adhesive element is present in a form that is compatible with the intended use of the sensor and the method, for example, a layer, a coating, a patch, or a brush. For example, the non-adhesive element could be a self-assembled monolayer, gel layer, polymer brush, or a suitable structure that is compatible with the intended use of the sensor and the method.

In some embodiments, the non-adhesive element is a polymer brush that is compatible with the intended use of the sensor and the method. The non-adhesive polymer brush element can be disposed on and in contact with the substrate, or intermediate layers can be present to provide desired functionality such as enhanced adhesion to the substrate. The non-adhesive polymer brush can be physically or chemically bonded to the substrate. The non-adhesive polymer brush can be continuous or discontinuous on the substrate. The non-adhesive polymer brush can be flat and conformal to the surface of the substrate (e.g., a flat layer disposed concentrically on a fiber substrate), or contoured (e.g., a layer or other shape thicker in some regions than in other regions).

A wide variety of materials can be used as the non-adhesive element, for example certain surfactants, amphiphiles, and polymers, either synthetic or naturally occurring, for example certain natural polymers such as cellulosics including hydroxyethyl cellulose or pullulan, or synthetic polymers, particularly hydrophilic synthetic polymers or copolymers containing hydrophilic functionality, including polyalkylene glycols (e.g., oligoethylene glycol, polyethylene glycol, polypropylene glycol or polyethylene-propylene glycol, polyethylene oxide, polypropylene oxide), polyvinylpovidone, polyoxazoline, polyzwitterions (such as poly((3-(methacryloylamino)propyl)-dimethyl(3-sulfopropyl) ammonium hydroxide), poly(2-methacryloloxyethylphosphorylcholine), poly polysulfobetaines, polycarbobetaines, etc), polypeptides, polyurethanes, acrylics including 2-hydroxyethylmethacrylate and methoxy- and hydroxy-capped oligoethylene glycol methacrylate, polyacrylamides including carboxybetaine acrylamide, polyesters, polyimide polyether ketone, polyvinyl chloride, or a combination of at least one of the forgoing natural and synthetic polymers. The nonadhesive material can be attached to the substrate in various forms, including adhered to the substrate by physical forces or chemically attached, for example by linkers, and can be water soluble or water-solvated. In an embodiment, the non-adhesive material is a polymer that is sterically repulsive to bacteria and is net charge neutral. The components of the non-adhesive element, for example, the natural or synthetic polymer, can be part of a polymer, crosslinked, grafted, end-grafted, or otherwise functionalized. The chains of the natural or synthetic polymer can be extended, in a random coil, folded, or partially extended. The components of the non-adhesive polymer brush, for example the natural or synthetic polymer, oligomer, or amphiphile, if not cross-linked, can have a molecular weight of about 0.15 to 200 kiloDaltons. Polymer brushes are often characterized by a high density of grafted chains. In another embodiment, the polymer is zwitterionic, for example polymers derived from betaines, phosphorylcholine-substituted methacrylic polymers, or vinyl benzene imidazole polymers. The non-adhesive element is repulsive to proteins and cells.

In some embodiments, the non-adhesive polymer brush comprises synthetic or naturally occurring polymers, wherein suitable natural polymers comprise cellulosics polymers including hydroxyethyl cellulose or pullulan, and wherein synthetic polymers comprise hydrophilic synthetic polymers or copolymers containing hydrophilic functionality, including polyalkylene glycols, polyvinylpovidone, polyoxazoline, polyzwitterions, polypeptides, polyurethanes, acrylics including 2-hydroxyethylmethacrylate and methoxy- and hydroxy-capped oligoethylene glycol methacrylate, polyacrylamides including carboxybetaine acrylamide, polyesters, polyimide polyether ketone, polyvinyl chloride, or a combination of at least one of the forgoing natural and synthetic polymers.

In some embodiments, the synthetic polymer is a polypropylene glycol (at higher molecular weights known as polypropylene oxide, PPO) or polyethylene glycol (at higher molecular weights known as polyethylene oxide, PEO), for example a polyethylene glycol having the formula

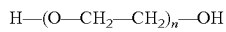

wherein n is about 3 to about 10,000. The polyethylene glycol can be grafted, or functionalized to modify a property thereof, and can be present as a polymer brush.

In a specific embodiment, the non-adhesive element comprises a polymer brush comprising poly(ethylene glycol) having weight average molecular weight of 133 to 100,000.

The adhesive element can be a modified portion of the non-adhesive polymer brush, for example the natural or synthetic polymer wherein discrete nanoregions of the polymer may have been modified (e.g., functionalized) to be adhesive to the target cells. Alternatively, the adhesive elements can be discrete molecules or particles associated with the non-adhesive polymer brush. Thus, the adhesive elements can be a natural polymer such as a polypeptide or a protein, chitosan, a synthetic polymer or polymer nanoparticle, including a cationic and/or hydrophobic synthetic polymer, or a cationic and/or hydrophobic dendrimer; or a cationically functionalized moiety, for example a cationically-functionalized hydrophobic synthetic polymer, a cationically-functionalized hydrophobic synthetic polymer particle, a cationically-functionalized dendrimer, a cationically-functionalized hydrophobic nanoparticle, or a canonically and/or hydrophobically-functionalized inorganic nanoparticle; or combination comprising at least one of the foregoing. The nanoregions or nanoparticles can be of any shape, regular or irregular. The regions or particles can have an average largest dimension of about 3 to about 100 nanometers (nm), specifically about 5 to about 50 nm.

In some embodiments the adhesive element is a polymer, a nanoparticle, a dendrimer, or a combination comprising at least one of the foregoing. The adhesive element can be a polypeptide, a protein, a hydrophobic synthetic polymer, a hydrophobic synthetic polymer particle, a cationic synthetic polymer, cationically-functionalized hydrophobic synthetic polymer, a cationically-functionalized hydrophobic synthetic polymer particle, a cationic dendrimer, a hydrophobic nanoparticle, a cationic nanoparticle, a cationically-functionalized nanoparticle, or combination comprising at least one of the foregoing.

In some embodiments, the adhesive element comprises a polymer comprising poly(L-lysine), preferably having a viscosity average molecular weight of about 5000 to about 50,000. In a specific embodiment, the polymer comprises a cationic poly-l-lysine chain having a viscosity average MW of about 15,000 to about 30,000, wherein the adhesive element is present at a surface density of about 1000 to about 80,000 elements/$\mu m^2$.

In other embodiments, the adhesive element is a cationically and/or hydrophobically functionalized nanoparticle comprising a metal, a metal oxide, or a ceramic core. In a specific embodiment, the adhesive element is an amine-functionalized silica nanoparticle. In another specific embodiment, the adhesive element is a cationically and/or hydrophobically-functionalized metal nanoparticle of Groups 10 to 11 of the Periodic Table of the Elements.

The adhesive elements may have a suitable surface density that is compatible with the intended use of the sensor and the method. In some embodiments, the surface density of the adhesive elements is about 1 element per square micrometer to about 50,000 elements per square micrometer.

In some embodiments, the targeted cell type is epithelial cells. In a specific embodiment, the targeted cell type is breast epithelial cells. These cells could be cancerous, pre-cancerous, or healthy breast epithelial cells. In other embodiments, the targeted cell types may be models for these epithelial cells including immortalized breast epithelial cell lines.

In some embodiments, the targeted cell type is MCF-10A, MCF-7, or TMX2-28 cells. In a specific embodiment, the target epithelial cells comprise MCF-10A (non-tumorigenic) cells, the adhesive elements comprise cationic poly-l-lysine chains having a viscosity average molecular weight of about 20,000 and the adhesive element has a surface density of about 2000 to about 3,500 elements per square micrometer, the non-adhesive element comprises a poly(ethylene glycol) brush, and the fluid is contacted with the engineered surface at a wall shear rate of 20 $s^{-1}$.

In another specific embodiment, the target epithelial cells are TMX2-28 cells, the adhesive elements comprise cationic poly-l-lysine chains having a viscosity average molecular weight of about 20,000 and the adhesive element has a surface density of about 1000 to about 1,800 elements per square micrometer, the non-adhesive element comprises a poly(ethylene glycol) brush, and the fluid is contacted with the engineered surface at a wall shear rate of 20 $s^{-1}$.

The fluid may be any suitable biological fluid, for example breast milk, saliva, sweat, urine, tears, semen, mucous, and vaginal cervical mucous, and blood. In a specific embodiment, the fluid is human breast milk.

The fluid may comprise biological materials other than the target cells. For example, the fluid can comprise proteins, fats, carbohydrates, lipids, electrolytes, or a combination comprising at least one of the foregoing.

Figure 2:
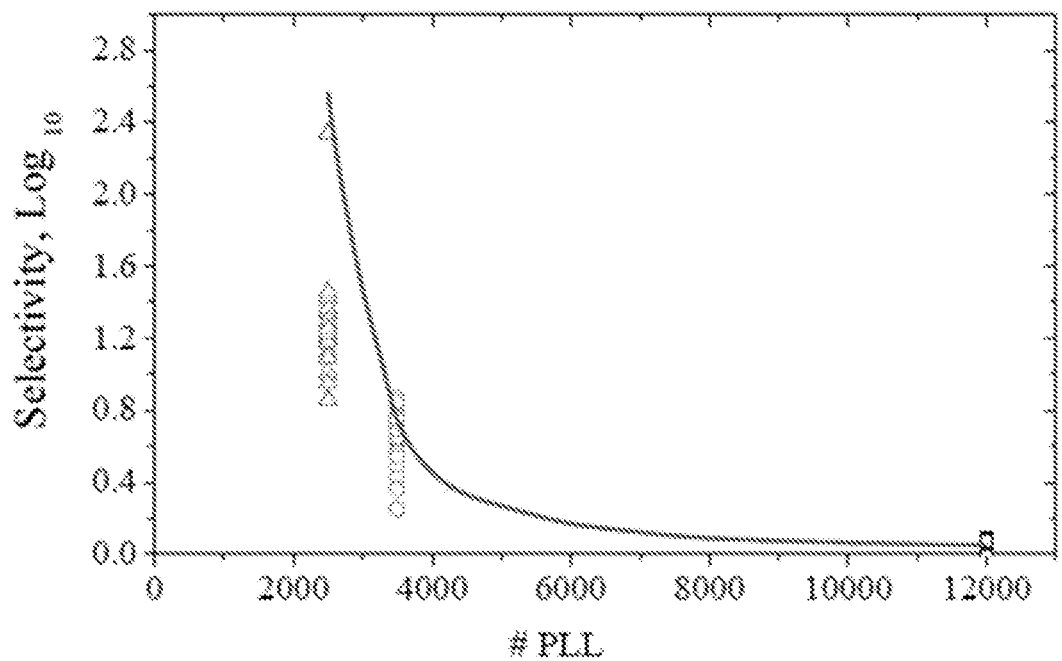
FIG. 2 is a plot of selectivity of adsorption of MCF-10A cells from a buffered suspension containing MCF-10A and Jurkat cells. Wall shear rate is 22 $s^{-1}$. X-axis is the nominal number of poly-l-lysine (PLL) coils per square micron on each test surface. It should be noted that the highest selectivity datum (where the y-axis is about 2.4) has 12 data points in that one spot. They are all on top of each other so they cannot be seen in the figure. This indicates that a very high degree of separation can be obtained by the engineered surfaces.

The sensors and methods enable selective capture of target cells without relying on bio-molecular recognition. In some embodiments, the selectivity of target cells captured using the sensors or methods is more than 20, more than 25, more than 30, more than 35, more than 40, more than 60, more than 80, more than 100, or more than 150. The present inventors have demonstrated that the engineered surfaces disclosed herein can provide selectivity even higher than 100 as shown in FIG. 2.

In a specific embodiment, the targeted cell type is breast epithelial cells, and the adhered cells are further subjected to epigenetic testing for breast cancer.

The foregoing and other embodiments are further illustrated by the following examples, which are not intended to limit the effective scope of the claims. All parts and percentages in the examples and throughout the specification and claims are by weight of the final composition unless otherwise specified.

Examples

Example 1—Selective Capture of Cells in Buffer

Engineered surfaces were developed to capture targeted cell types from flowing buffer in a laminar microfluidic-type apparatus. In this arrangement, a cell suspension was flowed past the test surface and the adhesive cell accumulation was monitored on a camera capable of taking micro-photographs.

The test surfaces were designed to exploit the general strategy of clustering adhesive surface functionality on an otherwise non-adhesive background surface. The adhesive surface clusters were nanoscale in size, on the order of 10 nanometer (nm). This was accomplished by using functionalized nanoscale objects. In this particular embodiment, polymer coils were used. Nanoparticles and dendrimers may also be used. The clustered adhesive functionality was cationic and the attractive interactions were electrostatic in nature. Clustered positive charge on the collecting surface was attractive to negatively charged groups on the surfaces of cells. In this example, each test surface contained a specified amount of randomly adsorbed cationic poly-l-lysine (PLL) chains. The remaining surface around the PLL coils was backfilled with a PEG (polyethylene glycol) brush. The PEG brush was engineered so that surfaces without the PLL coils were completely cell and protein repellant. Then the amount of embedded PLL coils was systematically varied. Preparation of such surfaces is disclosed in Gon, S., Bendersky, M., Ross, J. L. and Santore, M. M., Manipulating Protein Adsorption using a Patchy Protein-Resistant Brush. *Langmuir* 2010, 26 (14), 12147-12154; Gon, S. and Santore, M. M., Single Component and Selective Competitive Protein Adsorption in a Patchy Polymer Brush: Opposition between Steric Repulsions and Electrostatic Attractions, *Langmuir* 2011, 27 (4), 1487-1493; Gon, S. and Santore, M. M., Sensitivity of Protein Adsorption to Architectural Variations in a Protein-Resistant Polymer Brush containing Engineered Nano-scale Adhesive Sites, *Langmuir* 2011, 27, 15083-15091; Gon, S. and Santore, M. M., Interaction of Cationic Proteins and Polypeptides with Biocompatible Cationically-Anchored PEG Brushes, *Macromolecules* 2011, 44, 8161-8168; and Fang, B., Gon, S., Park, M. H., Kumar, K. N., Rotello, V. M., Nusslein, K. and Santore, M. M., Using Flow to Switch the Valency of Bacterial Capture on Engineered Surfaces Containing Immobilized Nanoparticles. *Langmuir* 2012, 28 (20), 7803-7810; and Fang and Santore, Coll. Surfaces B, 87(1), 109-115, 2011.

The results of several studies are summarized in FIG. 1, which compares the capture rates of different cell types from the fluid on individual surface compositions within this class of surfaces, for different amount of PLL incorporated into the surface. The plot shown in FIG. 1 is essentially an "engineering map" for surface design. Suspensions, each containing a single cell type, are studied in phosphate-buffered saline. The cell capture in such a study is interpreted as a predictor for how that cell type would behave in a mixture of cells. The y-axis indicates the rate of accumulation of each cell type on the surface. The inventors have generally found, at least for particles and other systems in which there are no specific interactions between particles and cell types, that such an approach is indeed a good predictor of adhesive capture behavior in multicomponent suspensions, a concept addressed further in FIG. 2.

In the engineering map illustrated in FIG. 1, for each cell type individually studied, the cell capture rate starts at zero, for surfaces containing low levels of PLL and then increases above a threshold. Importantly the threshold surface composition for the onset of adhesive capture is unique to each cell type. Thus, it is possible to engineer surfaces between the thresholds of cells in a suspension: Cell types with thresholds below the PLL loading on the engineered surface will be captured, albeit at a finite rate, while cell types having greater thresholds will flow past. The single cell-type studies in FIG. 1 suggest that surfaces in the composition range 2000-3500 PLL coils/$\mu m^2$ will separate MCF-10A cells from Jurkat T-cells by adhesively capturing the MCF-10A cells.

The MCF-10A cells were chosen as a model for non-tumorigenic breast epithelial cells of the type targeted for epigenetic testing for breast cancer, while the Jurkat cell line serves as a model for the lymphocytes present in breast milk (that need to be eliminated by purification before epigenetic tests are conducted.) The findings in FIG. 1 therefore constitute a highly desirable result in that they demonstrate that the surfaces interact differently with these two cell lines. FIG. 1 also shows the capture kinetics of two breast cancer cell lines: MCF-7 a commonly studied line and TMX2-28, a tamoxifen-selected clone of MCF-7, representing a treatment-resistant type. These two cell lines were chosen because they represent very similar lines and would be particularly challenging to discriminate with engineered surfaces of the present application. Interestingly, slight differences in the capture of these two cell types, from each other and from the non-tumorigenic MCF-10A line are evident. Therefore, from the results shown in FIG. 1 it is clear that these surfaces can distinguish tumorigenic and non-tumorigenic breast cell lines.

FIG. 2 explores the adhesive selectivity of the engineered surfaces for targeted cells when those cells are part of a multicomponent suspension (containing multiple cell types) in buffer. Such a study is different from the single-cell type studies in FIG. 1 where a comparison is made between different data sets, each with a single cell type. As an example, FIG. 2 details the behavior of buffered suspensions containing mixtures of MCF-10A and Jurkat T-lymphocytes, in roughly equal proportions. The mixed suspensions were passed over test surfaces and the capture of cells was monitored. Later, the captured cells were treated with a fluorescent antibody to Ep-CAM (Epithelial Cell Adhesion Molecule), to distinguish the epithelial and lymphocyte cells. The adhesive capture of the Jurkat and MCF-10A lines from the mixed cell suspension was studied on two test surface compositions (2500 PLL/$m^2$ and 3500 PLL/$m^2$, chosen based on guidance from FIG. 1) and a control surface composition containing 12,000 PLL/$m^2$. The selectivity is defined as the ratio of targeted (MCF-10A) to non-targeted (Jurkat) cells found on the surface of interest, normalized by the same ratio in bulk solution.

FIG. 2 summarizes the results for 5 different specimens of each test surface composition, where 6 different regions on each specimen were analyzed. Also, FIG. 2 includes the predicted capture selectivity for MCF-10A on surfaces where the PLL loading content was systematically increased. These predictions are based on the data in FIG. 1, and on the assumption that adhesive capture of the cells of interest is independent of the presence of other cells. The agreement between the expected and observed selectivity is excellent, but reflects some error in surface composition (x-axis, resolvable with analysis of the capture rate).

Further, from the data in FIG. 2, it is evident that there is an optimal range of surface compositions, or PLL loadings, to adhesively distinguish MCF-10A and Jurkat cell lines. In the limit of weak adhesion corresponding to low PLL surface loadings, cells fail to adhere. Conversely in the limit of strong adhesion corresponding to high PLL surface loadings, selectivity is compromised and different cell types adhere similarly, at their transport-limited rates. Thus at high surface loadings of PLL the selectivity is diminished.

Two important features of FIG. 2 are worth noting: First, for test surfaces containing 2500 PLL coils/$\mu m^2$, the selectivity to adhesively capture MCF-10A and reject Jurkat cells is extremely large (note the log 10 scale.) On twelve regions examined (the high blue triangle actually contains 12 points), only MCF-10A cells were found to adhere and Jurkat cells were completely rejected. Here the observed selectivity is infinite; however, it can be estimated, as a worst case, that if the next cell to be captured would be a Jurkat, and then this would give a finite but high selectivity, corresponding to one Jurkat in a bit more than 100 MCF 10A cells. The other surfaces with lower selectivities still performed satisfactorily, with about 1 Jurkat in order 30 total cells captured. These surfaces (with compositions of 2500 PLL/$m^2$) have near perfect selectivities, rivaling surfaces containing immobilized antibodies and complete eliminating of non-specific adhesion.

The second important feature of FIG. 2, in which cells absorb from a suspension containing multiple cell types, is its consistency with FIG. 1 in which suspensions contained only one cell type each. The quantitative agreement between the predicted and observed data in FIG. 2, albeit only with a limited number of data points, is an indicator that cell capture is controlled by single-cell-surface interactions. With negligible influence of cell-cell interactions on the capture process, single-cell suspension studies like those in FIG. 1 are powerful tools for surface design and have aided the inventors' choice of surfaces for more involved studies with mixed suspensions. Studies with mixed cell suspensions are more tedious because of their multiple steps to assay the different cell types after capture. To do such assays, standard procedures must be adapted to the surface conditions of the experiment and additional control studies run (as was done) to ensure proper functioning of the assay with each cell-type pair.

Without being bound by theory, it is believed that potentially important cell characteristics include surface charge, surface charge distribution, cell size, local curvature, and mechanical properties. A difference in any single one of these properties might produce high adhesive selectivity. Further, if the target cells differ in two or more of these properties, the potential for selective capture might be enhanced or compromised depending on whether each parameter favors or opposes the capture of one cell type.

Figure 3:
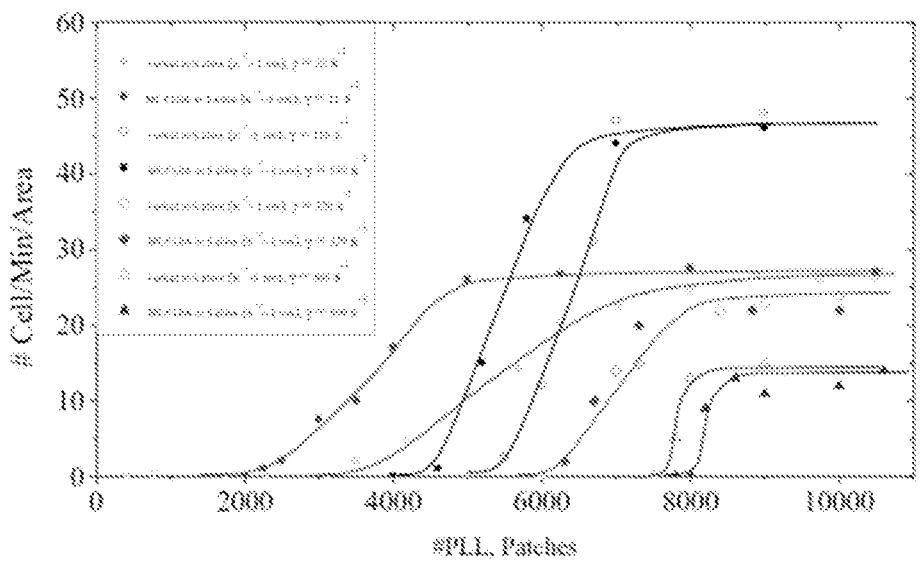
FIG. 3 is a plot showing influence of shear rate on capture of MCF10-A and Jurkat cells.

FIG. 3 summarizes an important and unexpected result: the influence of shear flow on capture. Analogous to FIG. 1, FIG. 3 plots the capture efficiency of MCF-10A and Jurkat Cells in buffer, comparing two of the data sets from FIG. 1 with additional studies also conducted over the full range of PLL surface loadings of interest, at progressively higher wall shear rates. The results show that increases in flow rate shift the adhesion thresholds to higher surface loadings (because stickier surfaces are needed to capture cells in opposition to increasing hydrodynamic forces). The influence of shear on the thresholds for the two cell types is, however, different. The thresholds for the MCF-10A cells shift more dramatically than the thresholds for the Jurkat cells. As a result the ranking of the adhesion thresholds, and therefore the selectivity, is inverted as the shear rate is increased from 22 to 500 $s^{-1}$. At low wall shear rates, the MCF-10A cells have the lower adhesion threshold. Selective capture favors MCF-10A cells over Jurkat cells, as confirmed in FIG. 2. At high shear rates approaching 500 $s^{-1}$, the selectivity is reversed and FIG. 3 predicts that surfaces with PLL loadings engineered near 7600 PLL/$um^2$ will adhesively capture Jurkat cells while rejecting MCF-10A cells.

Notably, at intermediate wall shear rates of about 320 $s^{-1}$, the adhesive selectivity is lost. Slight differences in cell size are a possible explanation for this behavior as hydrodynamic forces typically scale as sphere-diameter squared, potentially amplifying the effect of cell diameter. The switching of selectivity for one cell type or another is a powerful tool because it enables the same surface to target different analyte cells, depending on process conditions. The observation of hydrodynamic switching of selectivity for a targeted species is also significant because it may enable the impact of cell size on selectivity to be decoupled from the impact of surface charge on selectivity.

Example 2—Discriminating Cell Lines Re-Suspended in the Supernatant of Breast Milk The ability to selectively capture cells directly from biological fluids is challenging because molecules from the fluid can interfere with or alter cell-surface interactions. While the effect might be slight for surfaces which exploit recognition of biomolecular fragments (antibodies or DNA for instance), technologies such as the clustered cationic functional surfaces described herein (which exploit molecularly non-specific interactions) face a greater challenge). It is important that engineered surfaces resist fouling by the molecular components of the biological fluid of interest. In the case of breast milk this includes proteins, fats, and other molecules, not all of which are known and which are highly varied. While the brushy surfaces without immobilized PLL coils tend to repel these molecules sterically, the highly cationic PLL molecules tend to adhere other species, especially those that are anionic. Therefore surfaces that exploit the cationic functionality of immobilized PLL coils must present the PLL coils within the PEG brush in ways to limit access to unwanted molecules from the solution. The surface designs in this study embed the PLL coils within the PEG brush to potentially shield molecular interactions. The selective cell capture results from Example 1 have demonstrated that the surface design strategy allows sufficiently strong surface-cell interactions to facilitate capture of the targeted cells.

Figure 4:
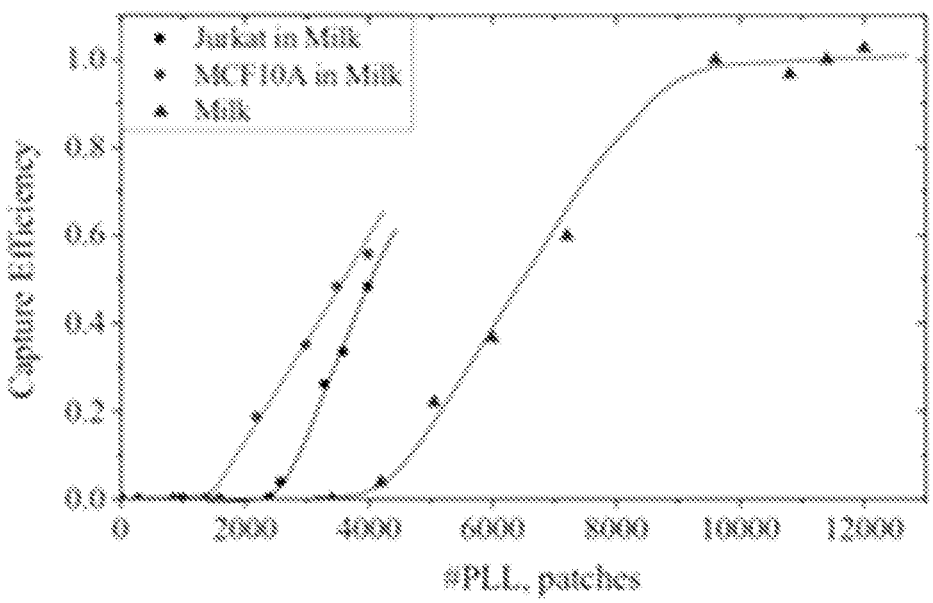
FIG. 4 is a plot of efficiencies of capturing Jurkat and MCF-10A cells from breast milk serum, mixed 50% with phosphate buffered saline to regulate pH. The x-axis describes the density of PLL coils/$\mu m^2$.

A milk serum was obtained when cells were removed from donated human breast milk by centrifugation. The separate fatty layer was additionally skimmed off the top to ensure a relatively uniform suspension remaining. All milk serum specimens were then diluted 50:50 by volume in phosphate buffer, in order to maintain a consistent pH among specimens. FIG. 4 includes the capture efficiencies of molecules and non-cellular material from this milk serum, defined as the mass accumulation rate on a test surface (with its finite loading of PLL coils) relative to the mass accumulation rate on a control surface containing a densely cationic saturated layer of adsorbed PLL. Importantly, FIG. 4 shows negligible adsorption on surfaces comprising only a PEG brush, and on surfaces containing relatively low PLL loadings in the PEG brush. Above a threshold PLL loading near 4200 PLL/$m^2$, however, material adsorbs to the surface from the milk serum. This adsorption increases with further amounts of PLL on the collector. The surfaces that adsorb molecules from the milk are those well above the adhesion thresholds of the various cells, in FIG. 1, illustrating the potential for surface designs where the PLL loading on the collector is sufficient to adhesively capture targeted cells while resisting fouling from the components of the milk serum.

Two separate additional studies, summarized in FIG. 4, further explore the capture of MCF-10A and Jurkat cells directly from serum. Also included in this graph is the adsorption of the milk serum itself. Both cell types were found to be captured on the series of test surfaces in a manner qualitatively similar to their behavior in buffer: no cell capture occurred on surfaces with the lowest PLL loadings while capture was rapid on collectors densely functionalized with PLL. There were sharp, cell-line specific thresholds for the onset of capture two types of cells. The window of surface design between the two thresholds is expected to be sharply selective for MCF-10A cells. FIG. 4 reports the interesting observation that in the presence of milk serum the two thresholds are shifted relative to the threshold surface compositions in buffer. This may be a result of material adhering from the serum directly to the cells, or it may be a result of modified surface-cell interactions at different ionic strengths within milk compared with the controlled conditions in the buffer, from FIG. 1.

All ranges disclosed herein are inclusive of the endpoints, and the endpoints are independently combinable with each other. Each range disclosed herein constitutes a disclosure of any point or sub-range lying within the disclosed range. The use of the terms "a" and "an" and "the" and similar referents in the context of describing the invention (especially in the context of the following claims) are to be construed to cover both the singular and the plural, unless otherwise indicated herein or clearly contradicted by context. "Or" means "and/or."

All cited patents, patent applications, and other references are incorporated herein by reference in their entirety. However, if a term in the present application contradicts or conflicts with a term in the incorporated reference, the term from the present application takes precedence over the conflicting term from the incorporated reference.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

The invention claimed is:

1. A method of selectively capturing a targeted cell type from a fluid comprising the targeted cell type and a non-targeted cell type, the method comprising
   providing an engineered surface comprising
      a substrate,
      a non-adhesive element disposed on at least a portion of the substrate, wherein the non-adhesive element is non-adhesive to at least the non-targeted cell type, and
      an adhesive element disposed on the substrate, wherein the adhesive element has cationic functionality and is adhesive to the targeted cell type without use of bio-molecular recognition, wherein the surface density of the adhesive elements is about one element per square micrometer to about 50,000 elements per square micrometer; and
   contacting the engineered surface with the fluid at a wall shear rate from 10 $s^{-1}$ to 500 $s^{-1}$,
   wherein the surface and the wall shear rate of the fluid are effective to selectively capture at least a portion of the targeted cell type, from the fluid comprising the targeted cell type and a non-targeted cell type, to the engineered surface, wherein the selectively captured targeted cell type is captured to the engineered surface without bio-molecular recognition.

2. The method of claim 1, wherein the targeted cell type comprises epithelial cells and the engineered surface and shear rate are selected for selectively capturing the epithelial cells.

3. The method of claim 1, wherein the targeted cell type comprises lymphocyte cells and the engineered surface and shear rate are selected for selectively capturing the lymphocyte cells.

4. The method of claim 1, wherein the targeted cell type is an epithelial cell type or a leukocyte cell type and the engineered surface and shear rate are selected for selectively capturing the epithelial cell type or the leukocyte.

5. The method of claim 1, wherein the targeted cell type comprises an epithelial cell type or a leukocyte cell type from a patient or from primary culture.

6. The method of claim 4, wherein the target cell type comprises breast epithelial cells.

7. The method of claim 6, wherein the target epithelial cells comprise MCF-10A breast epithelial cells, the adhesive element comprises cationic poly-l-lysine chains having a viscosity average molecular weight of about 20,000 and the adhesive element has a surface density of about 2000 to about 3,500 elements per square micrometer, the non-adhesive element comprises a poly(ethylene glycol) brush, and the fluid is contacted with the engineered surface at a wall shear rate of 20 $s^{-1}$.

8. The method of claim 6, wherein the target epithelial cells are TMX2-28 epithelial cells, the adhesive elements comprise cationic poly-l-lysine chains having a viscosity average molecular weight of about 20,000 and the adhesive element has a surface density of about 1000 to about 3,000 elements per square micrometer, the non-adhesive element comprises a poly(ethylene glycol) brush, and the fluid is contacted with the engineered surface at a wall shear rate of 20 $s^{-1}$.

9. The method of claim 1, wherein the fluid is a biological fluid, selected from the group consisting of breast milk, saliva, sweat, urine, tears, semen, mucous, vaginal cervical mucous, blood, blood serum, and combinations thereof.

10. The method of claim 1, wherein a selectivity of the method for capturing the targeted cell type compared to the non-targeted cell type is more than 20.

11. The method of claim 1, wherein the non-adhesive element is a layer, coating, patch, brush, self-assembled monolayer, gel layer, or polymer brush, and is selected based on the targeted cell type.

12. The method of claim 1, wherein the non-adhesive element is at least one of repulsive to proteins, or repulsive to cells.

13. The method of claim 1, wherein the non-adhesive element is repulsive to the targeted cell type.

14. The method of claim 1, wherein the non-adhesive element is a polymer brush disposed on and in contact with the substrate or with an intermediate layer.

15. The method of claim 11, wherein the polymer brush comprises poly(ethylene glycol) having the formula H—(O—CH$_2$—CH$_2$)$_n$—OH wherein n is about 3 to about 10,000.

16. The method of claim 1, wherein the non-adhesive element or component thereof comprises a surfactant, amphiphile, oligomer, synthetic polymer, naturally occurring polymer, or a combination comprising at least one of the foregoing.

17. The method of claim 1, wherein the non-adhesive element is disposed on the substrate by a physical force.

18. The method of claim 1, wherein the non-adhesive element is disposed on the substrate by a chemical attachment.

19. The method of claim 18, wherein the chemical attachment comprises a linker group.

20. The method of claim 1, wherein a wall shear rate at which the fluid is contacted with the engineered surface is about 10 $s^{-1}$ to about 400 $s^{-1}$.

21. The method of claim 1, wherein the targeted cell type is from a patient.

22. The method of claim 1, wherein the targeted cell type is from a primary culture.

23. The method of claim 1, wherein the targeted cell type is from an immortalized cell culture.

24. The method of claim 1, wherein the adhesive element is a polymer, a nanoparticle, a dendrimer, or a combination comprising at least one of the foregoing.

25. The method of claim 24, wherein the adhesive element is a polypeptide, a protein, a hydrophobic synthetic polymer, a hydrophobic synthetic polymer particle, a cationic synthetic polymer, a cationically-functionalized hydrophobic synthetic polymer, a cationically-functionalized hydrophobic synthetic polymer particle, a cationic or cationically-functionalized dendrimer, a hydrophobic nanoparticle, a cationic nanoparticle, a cationically-functionalized nanoparticle, or a combination thereof.

26. The method of claim 25, wherein the adhesive element is a cationically and/or hydrophobically functionalized nanoparticle comprising a metal, a metal oxide, or a ceramic core, an amine-functionalized silica nanoparticle, or a cationically and/or hydrophobically-functionalized metal nanoparticle of Groups 10 to 11 of the Periodic Table of the Elements.

27. The method of claim 24, wherein the adhesive element comprises a homopolymer comprising poly(L-lysine).

28. The method of claim 1, wherein the adhesive element is a modified portion of a non-adhesive polymer brush, a molecule associated with the non-adhesive polymer brush, or a discrete particle associated with the non-adhesive polymer brush.

29. The method of claim 28, wherein the adhesive element is a natural polymer, a synthetic polymer, or a polymer nanoparticle.

30. The method of claim 29, wherein the adhesive element is a polypeptide, a protein, or chitosan.

31. The method of claim 29, wherein the adhesive element is a cationically functionalized moiety selected from a cationically-functionalized hydrophobic synthetic polymer, a cationically-functionalized hydrophobic synthetic polymer particle, a cationically-functionalized dendrimer, a cationically-functionalized hydrophobic nanoparticle, or a canonically or hydrophobically-functionalized inorganic nanoparticle, or a combination comprising at least one of the foregoing.

32. The method of claim 30, wherein the adhesive element is a nanoparticle or nanoregion having an average largest dimension of about 3 to 100 nm.

33. The method of claim 1,
wherein the non-adhesive element is a polymer brush disposed on and in contact with the substrate or with an intermediate layer, and
wherein the adhesive element is a polypeptide, a protein, a hydrophobic synthetic polymer, a hydrophobic synthetic polymer particle, a cationic synthetic polymer, a cationically-functionalized hydrophobic synthetic polymer, a cationically-functionalized hydrophobic synthetic polymer particle, a cationic or cationically-functionalized dendrimer, a hydrophobic nanoparticle, a cationic nanoparticle, a cationically-functionalized nanoparticle, or a combination thereof.

34. The method of claim 1, wherein the fluid is a biological fluid.

35. The method of claim 34, wherein the engineered surface is non-fouling by molecular components of the biological fluid.

36. The method of claim 1, wherein the selectivity of the method for capturing the targeted cell type compared to the non-targeted cell type is more than 3.

37. The method of claim 1, wherein the selectivity of the method for capturing the targeted cell type compared to the non-targeted cell type is more than 100.

38. The method of claim 1, wherein the surface density of the adhesive elements is about 1000 elements per square micrometer to about 50,000 elements per square micrometer.

* * * * *